United States Patent [19]

Uzgiris

[11] 4,171,956
[45] Oct. 23, 1979

[54] LASER IMMUNOASSAY

[75] Inventor: Egidijus E. Uzgiris, Schenectady, N.Y.

[73] Assignee: General Electric Company, Schenectady, N.Y.

[21] Appl. No.: 805,976

[22] Filed: Jun. 13, 1977

[51] Int. Cl.² .................... G01N 33/16; G01N 21/22; H01S 3/23

[52] U.S. Cl. ................................ 23/230.3; 23/230 B; 250/461 B; 331/DIG. 1; 356/318; 424/8; 424/12; 422/80

[58] Field of Search .......................... 23/230 B, 230.3; 356/85; 331/DIG. 1; 250/461 B; 424/8, 12

[56] References Cited

U.S. PATENT DOCUMENTS

| 3,939,350 | 2/1976 | Kronick | 250/365 |
| 3,984,533 | 10/1976 | Uzgiris | 424/12 |
| 4,011,044 | 3/1977 | Uzgiris | 23/253 R X |
| 4,020,151 | 4/1977 | Bolz | 23/230 B |
| 4,036,946 | 7/1977 | Kleinerman | 424/8 |
| 4,058,732 | 11/1977 | Wieder | 250/461 B |

OTHER PUBLICATIONS

Fairbank et al., Jour. of the Optical Society, 65, 199–204 (1975).
Wang, Combustion Science and Tech., 13, 212 (1976).
Hurst et al., Applied Physics Letters, 30, 229–231 (1977).
Chemical Abstracts, 75:86614m (1971).
Chemical Abstracts, 83:26071n (1975).

*Primary Examiner*—Sidney Marantz
*Attorney, Agent, or Firm*—Nathan D. Herkamp; Joseph T. Cohen; Paul R. Webb, II

[57] ABSTRACT

An immune assay for tracing processes and reactions employs a narrow band laser tuned to the absorption line of a tracer isotope coupled chemically to a carrier molecule of protein. The carrier molecule is reacted with another molecule, the reaction products are vaporized, and resonance fluorescence from the tracer isotope illuminated by the laser is measured. Amplitude of the fluorescence signal provides a direct measure of the number of isotope-tagged molecules present after the reaction of interest.

10 Claims, 7 Drawing Figures

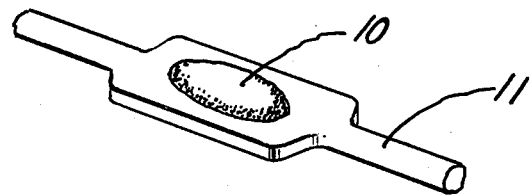
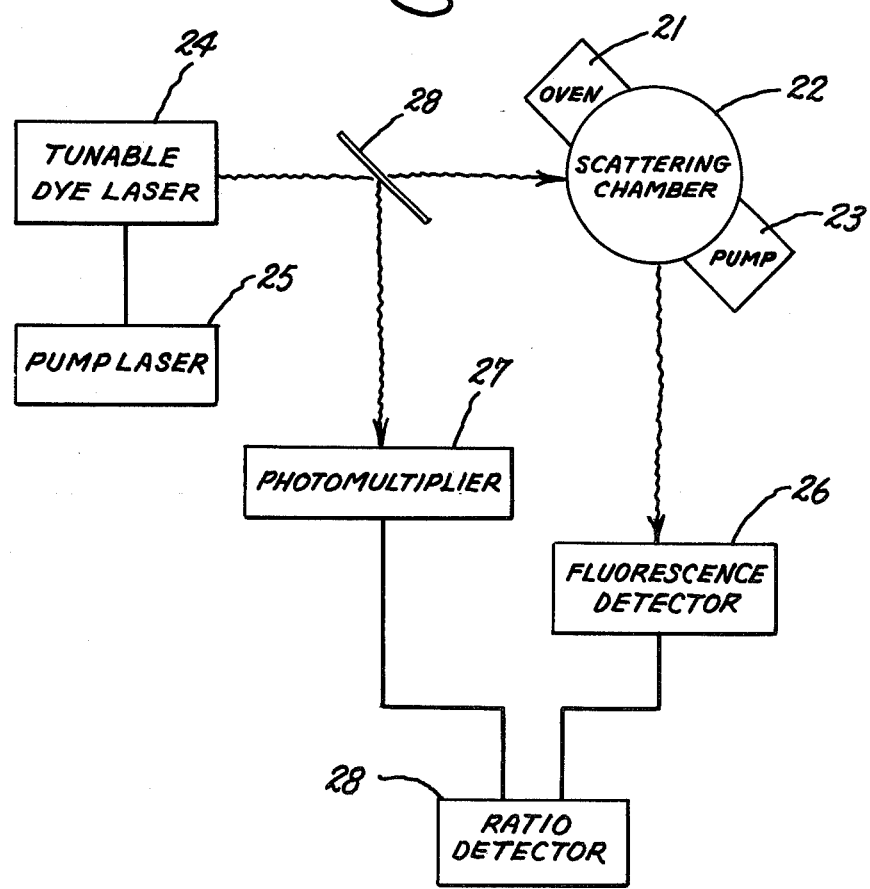

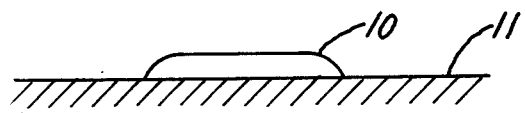
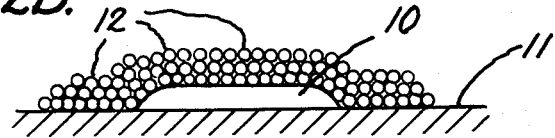
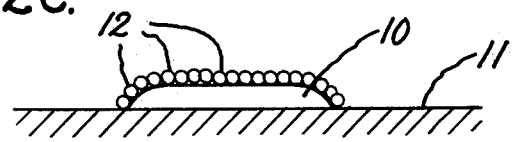
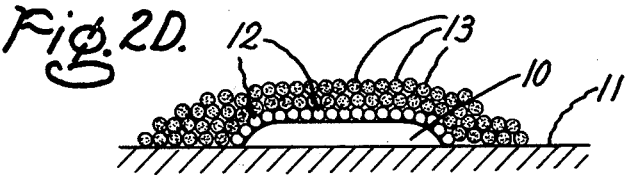
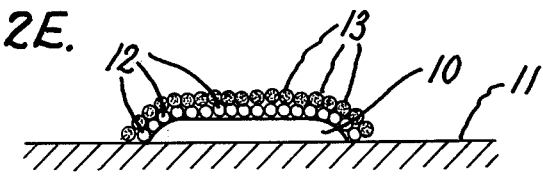

LASER IMMUNOASSAY

INTRODUCTION

This invention relates to the analytical technique of counting specific molecules by detecting isotopes bound thereto, and more particularly to a method and apparatus for performing such analysis by employing a narrow band laser.

Radioisotopes are widely used to trace processes and reactions. One particularly important expression of these techniques is in the method of radioimmune assay which combines immune reactions with radioactive labeling to test for infinitesimally small amounts of certain proteins and enzymes. For example, by labeling an antigen with a radioactive isotope, minute quantities (on the order of picograms or $10^{-12}$ grams) of antigen after an immune reaction with an antibody may be detected quickly and rapidly by employing a gamma radiation counter or scintillation detector. These radioimmunoassay techniques are dependent on radioactive decay. However, radioactive decay has several drawbacks associated with it in that only a small fraction of the unstable isotope atoms contribute to a decay signal at any one time and, of course, each of the unstable atoms can undergo decay only once.

Fairbank et al., in "Absolute Measurement of Very Low Sodium-Vapor Densities Using Laser Resonance Fluorescence", *Journal of the Optical Society of America*, 65, 199-204, February, 1975, showed that 100 atoms of sodium per cubic centimeter could be detected by illuminating a test volume with narrow band laser radiation tuned to the sodium-absorption line and measuring the resulting fluorescene. One principle reason for this high sensitivity is that a single atom can resonantly scatter a photon repeatedly and all atoms can contribute to the fluorescence signal. Use of a tunable narrow band laser as the illuminating source makes it possible to excite only the atomic species of interest without exciting any accompanying elements. The large ratio of fluorescence cross-sections to Rayleigh scattering cross-sections for atoms, typically $10^{12}$, allows detection of very minute quantities of a particular element in the presence of other matter. The present invention exploits this capability as the basis for creating a new immunoassay technique.

Accordingly, one object of the invention is to provide a method and apparatus for tracing processes and reactions with a high degree of sensitivity.

Another object is to provide a method and apparatus for performing immunoassays without need for monitoring radiation produced by radioactive decay.

Another object is to provide a method for performing laser immunoassays while minimizing the obscuring effects of Rayleigh scattering on the measurements being made.

Briefly, in accordance with a preferred embodiment of the invention, a method of performing a laser immunoassay comprises coupling a tracer isotope chemically to carrier molecules, and reacting the carrier molecules with a biological substance to be tested. The reaction products are thereafter separated from the reactants, vaporized, and irradiated with a narrow waveband of coherent light at the wavelength of the tracer isotope absorption line. Amplitude of resonance fluorescence emitted by the irradiated vaporized reaction products is measured to provide an indication of the number of carrier molecules combined with the tracer isotope that are present among the reaction products.

The features of the invention believed to be novel are set forth with particularity in the appended claims. The invention itself, however, both as to organization and method of operation, may best be understood by reference to the following description taken in conjunction with the accompanying drawings in which:

FIG. 1 illustrates a support for a protein to undergo laser immunoassay in the system of the instant invention;

FIGS. 2A-2E illustrate the process steps of coating a substrate with biological substances in order to practice the laser immunoassay of the instant invention; and FIG. 3 is a block diagram of apparatus employed in practicing the instant invention.

DESCRIPTION OF TYPICAL EMBODIMENTS

In performing the laser immunoassay of the instant invention, a monomolecular layer of a protein, such as an antigen 10, is adsorbed on a substrate comprising a tungsten wire or rod 11 of appropriate shape and surface area, as shown in FIG. 1. As an example, antigen 10 may be coated onto wire 11, as shown in FIG. 2A, by immersion of the wire, for example, into a 1% solution of bovine serum albumin (or BSA) antigen in physiological saline (0.154 Normal) and allowing incubation in the solution for about one minute. After removal of the BSA antigen monolayer-coated wire from the solution, it is rinsed with distilled water to remove nonadsorbed antigen and dried with compressed air, leaving a monomolecular layer of antigen 10 atop wire 11. Suspected rabbit anti-bovine serum albumin, diluted volumetrically in the range of 1:1 to about 1:10,000 in physiological saline, is dropped onto the BSA antigen-coated tungsten wire, as shown in FIG. 2B and incubated for about two minutes. The BSA antigen, being specific to rabbit anti-bovine serum albumin antibody complexes with these antibodies 12, if any exist in the solution dropped onto the BSA antigen-coated tungsten. The coated tungsten wire is then rinsed with distilled water to remove all noncomplexed molecules of the suspected anti-bovine serum albumin and dried with compressed air, leaving a monomolecular layer of antibodies 12 atop monomolecular layer of antigen 10, as shown in FIG. 2C, assuming that serum albumin 12 actually is the suspected rabbit anti-bovine serum albumin.

The coated tungsten wire shown in FIG. 1 is then coated with carrier molecules 13, as shown in FIG. 2D, by being immersed in a third solution including carrier molecules, each carrier molecule being a tagged antibody to the antibody to BSA antigen, which, in this particular case, comprises an antibody obtained through immunization of an animal other than a rabbit (e.g. goat), tagged with a tracer material that has appropriate ultraviolet or visible radiation absorption lines. One such material is iodine, it being common practice in performing radioimmunoassays to tag antibodies with radio-isotopes of iodine; i.e., with $^{131}I$ or $^{125}I$, as noted, for example, in C. Ling U.S. Pat. No. 4,012,494 issued Mar. 15, 1977. Immersion in the third solution for about 15-30 minutes is sufficient to permit incubation where the antibody concentration is in the typical range of 10 micrograms/milliliter—1 milligram/milliliter. Again the coated tungsten wire is rinsed with distilled water to remove the noncomplexed carrier molecules and dried with compressed air, leaving a monomolecular layer of carrier molecules 13, shown in FIG. 2E, coated atop antibodies 12.

After the tungsten wire has been exposed, sequenially, to the three different types of biological particles in the manner described, it is processed in the apparatus shown in FIG. 3. It should be noted, however, that by tagging the original antibodies 12, the subsequent steps performed to deposit a monomolecular layer of carrier molecules 13 thereon may be omitted, and the wire thus coated is processed in the apparatus shown in FIG. 3. This would result in a direct immunoassay, as opposed to the previously-described triple monomolecular layer deposition which constitutes an indirect assay. In either instance, the coated wire is heated in source oven 21 to vaporize the protein constituents thereon so as to free the atomic species of interest. In the alternative, a high power ultraviolet laser pulse at a wavelength of about 3800 Å from a nitrogen laser such as pump laser 25 could suffice to break up the protein sample on the tungsten wire and free the attached atomic species used for labeling the protein. Whether heated in oven 21 or irradiated by a laser pulse, the vaporized constituents pass into a scattering chamber 22 which is pumped down to vacuum pressures by vacuum pump 23.

Irradiation of the vaporized protein constituents within scattering chamber 22 is performed by a narrow band laser source such as a tunable dye laser 24 pumped by nitrogen pump laser 25. A high power radiation pulse from dye laser 24 enters scattering chamber 22 through a transparent window therein (not shown). Use of a tunable narrow band laser 24 makes it possible to excite only the atomic species of interest while not exciting any accompanying elements. The beam from dye laser 24 produces resonance fluorescence of the iodine isotope, allowing absolute measurements of the iodine vapor density to be made. That is, a fluorescence detector 26, such as a photomultiplier tube, responds to the fluoresence through another transparent window (not shown) in scattering chamber 22. Amplitude of the photomultiplier output signal is compared to amplitude of the output signal of laser 24, as sensed by a second photomultiplier 27 responsive to light reflected directly from dye laser 24 by a beam splitter 28 situated in the path of the incident beam of laser 24 between laser 24 and scattering chamber 22. Output signals from photomultipliers 26 and 27 are supplied to a ratio detector circuit 28 which provides an indication of the ratio of amplitudes sensed by each of photomultipliers 26 and 27. The amplitude ratio of output signals produced by photomultipliers 26 and 27 provides a convenient measure of the number of tagged molecules present in scattering chamber 22 after the reaction of interest, and a very small number of such molecules can thereby be measured.

In a gaseous sample, the resonance fluorescence from any particular gaseous species must compete with light scattered from background atoms not undergoing fluorescence. This scattering of light from background atoms is known as Rayleigh scattering. Cross-sections for Rayleigh scattering range from, for helium, $\sigma=3\times10^{-30}$ cm$^2$ sterad$^{-1}$, the lowest, to, for xenon, $\sigma\sim1\times10^{-27}$, one of the highest. This is pointed out by C. P. Wang in *Combustion Science and Technology*, 13, page 212. Resonance absorption cross-sections can be nearly $10^{16}$ times larger. Typical values for electronic transitions of atomic and molecular species are $10^{-12}$ cm$^2$ sterad$^{-1}$ to $10^{-16}$ cm$^2$ sterad$^{-1}$ (see page 213 of Wang). These parameters set the limits on design and sensitivity. The Rayleigh scattering, in some instances, can largely be eliminated by exciting to a second higher level and observing the cascade transitions from the first, while using a filter to block the primary radiation.

If a working area of 1 cm$^2$ on the tungsten wire shown in FIG. 1 is employed, 10% coverage of that area with labeled (i.e. tracer) antibody molecules would require about $10^{11}$ molecules. Assuming a $10^{-6}$ efficiency in label atoms compared to protein atoms present, then along with, say, $10^{11}$ signal atoms, a burst of $10^{11}/10^{-6}$ or $10^{17}$ atoms of background gas is produced. If the ratio of Rayleigh scattering cross-section to resonance absorption cross-section is $10^{-14}$, then $10^{17}\times10^{-14}=10^3$, so that the effective signal atom density would be $10^{11}/10^3$ or $10^8$ larger. Thus very high sensitivity or very tiny surface areas of tungsten could be examined. A $10^{-3}$ surface coverage of $10^{-3}$ cm$^2$ would still provide $10^9$ label atoms/cm$^2\times10^{-3}$ cm$^2$ or $10^6$ label atoms with essentially no background atoms.

Background pressure requirements are indicated in Table I below.

TABLE I

| Background Pressure (Torr) | Background Atoms/cc | Effective Background Atoms/cc (i.e., Atoms/cc $\times$ $10^{-14}$) |
|---|---|---|
| 760 | $2.7\times10^{19}$ | |
| 1 | $3.6\times10^{16}$ | $3.6\times10^{2}$ |
| $10^{-3}$ | $3.6\times10^{13}$ | $3.6\times10^{-1}$ |
| $10^{-5}$ | $3.6\times10^{11}$ | $3.6\times10^{-3}$ |

Therefore, in a 100 cc chamber, the effective background for $10^{-3}$ Torr would be $3.6\times10^{1}$ atoms. This is a satisfactory starting point for measurements.

A still further improvement over the limits of detection set forth above may be achieved by employing specific laser excitation followed by ionization of the excited atoms or molecules, in the manner described by Hurst et al., "A Demonstration of One-Atom Detection", *Applied Physics Letters*, 30, 229-231, Mar. 1, 1977. In this approach, two lasers would be used, with photons of energy $h\nu_1$ promoting from a ground state to a low-lying excited state, then photons of energy $h\nu_2$ promoting to a higher lying bound state. In the resonance ionization spectroscopy technique, at least one of the photons must ionize the higher excited state. This approach altogether eliminates the background contributed by Rayleigh scattering, allowing measurements to be obtained with higher sensitivity.

In the foregoing description of the invention, reference has been made to first, second and third immunologically reactive biological particles, the second particles being specific to the first and the third being specific to the second. These particles were identified as antigens, antibodies, and tagged antibodies, respectively. It will be appreciated, however, that the invention is not limited to this order of application of the biological particles on the substrate, nor is it limited to use only with the particles described as examples; indeed the invention is useful with virtually any combination of biological particles that will react or combine with each other. This also holds true for the direct immunoassay process.

The foregoing describes a method and apparatus for tracing processes and reactions with a high degree of sensitivity. Immunoassays may be performed without need for monitoring radiation produced by radioactive decay. The laser immunoassays of the invention are performed while minimizing the obscuring effects of Rayleigh scattering on the measurements being made.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

I claim:

1. A method of performing a laser immunoassay comprising:
   coupling a tracer isotope chemically to carrier molecules;
   reacting said carrier molecules with a biological substance to be tested so as to produce reaction products;
   vaporizing said reaction products;
   irradiating said vaporized reaction products with a narrow waveband of coherent light at the wavelength of the absorption line of said tracer isotope; and
   measuring amplitude of resonance fluorescence emitted by the irradiated vaporized reaction products as an indication of the number of carrier molecules combined with said tracer isotope that are present among said reaction products.

2. The method of claim 1 including the step of ionizing said reaction products following vaporization thereof.

3. The method of claim 1 wherein the step of reacting said carrier molecules with a biological substance to be tested comprises:
   applying to a substrate a first solution containing a protein specific to said biological substance so as to coat said substrate with a monomolecular layer of said protein;
   applying to the coated substrate a second solution suspected of containing said biological substance to cause complexing with said protein layer of molecules of said biological substance which may be present in said second solution; and
   applying to the coated substrate a third solution containing said carrier molecules, each of said carrier molecules being specific to, and complexing with, molecules of said biological substance complexed with said protein layer.

4. The method of claim 3 including the step of ionizing said reaction products following vaporization thereof.

5. The method of claim 1 wherein said tracer isotope comprises an isotope of iodine and wherein said vaporized reaction products are irradiated with coherent light at substantially 3800 angstroms wavelength.

6. The method of claim 1 wherein the step of measuring amplitude of resonance fluorescence comprises determining amplitude of resonance fluorescence relative to amplitude of said narrow waveband of coherent light at the wavelength of the absorption line of said tracer isotope.

7. The method of claim 6 wherein said tracer isotope comprises an isotope of iodine and wherein said vaporized reaction products are irradiated with coherent light at substantially 3800 angstroms wavelength.

8. The method of claim 7 including the step of ionizing said reaction products following vaporization thereof.

9. A method of performing a laser immunoassay comprising:
   coupling a tracer isotope chemically to molecules of a predetermined substance in a first solution;
   applying said first solution to a substrate coated with a monomolecular layer of a protein specific to said molecules so as to produce reaction products by allowing said molecules to complex with the protein layer;
   vaporizing said reaction products;
   irradiating said vaporized reaction products with a narrow waveband of coherent light at the wavelength of the absorption line of said tracer isotope; and
   measuring amplitude of resonance fluorescence emitted by the irradiated vaporized reaction products as an indication of the number of said molecules that have complexed with said protein layer.

10. The method of claim 9 including the step of ionizing said reaction products following vaporization thereof.

* * * * *